United States Patent [19]

Aoyagi

[11] 4,255,142
[45] Mar. 10, 1981

[54] CUTTING INSTRUMENT FOR A ROOT CANAL FILLER IN DENTAL TREATMENT

[76] Inventor: Mitsuhiro Aoyagi, 45-15 Nankoudai-Higashi, 1-chome, Izumi-shi, Miyagi-ken, Japan

[21] Appl. No.: 33,785

[22] Filed: Apr. 27, 1979

[30] Foreign Application Priority Data

May 15, 1978 [JP] Japan ............................ 53/64829[U]

[51] Int. Cl.³ ...................... A61C 19/00; A61C 19/04
[52] U.S. Cl. ........................................ 433/72; 433/75;
433/49; 83/522; 83/648; 269/9
[58] Field of Search ...................... 433/49, 51, 72, 75,
433/102, 144, 157, 163, 224, 229; 83/522, 648;
30/109, 124; 269/9, 43; 131/25

[56] References Cited

U.S. PATENT DOCUMENTS

| 174,836 | 3/1876 | Montejo | 83/522 |
|---|---|---|---|
| 197,901 | 12/1877 | Sargent | 83/522 |
| 217,351 | 7/1879 | DuBrul | 83/522 |
| 871,983 | 11/1907 | Cohen | 131/250 |
| 1,417,237 | 5/1922 | Evans | 433/75 |
| 1,459,077 | 6/1923 | Winans | 131/250 |
| 1,986,025 | 1/1935 | Stecher | 269/9 |
| 2,215,122 | 9/1940 | Hess | 269/9 |
| 2,655,259 | 10/1953 | Davoren | 83/648 |
| 3,358,826 | 12/1967 | Siegel | 433/102 |

Primary Examiner—Gene Mancene
Assistant Examiner—John J. Wilson
Attorney, Agent, or Firm—Jordan and Hamburg

[57] ABSTRACT

A base portion has an upper surface on which are formed slots for receiving root canal fillers. The slots are graduated whereby the length of each root canal filler can be adjusted easily. The base portion is provided with a cover plate for pressing and fixing the root canal fillers placed in the slots, the cover plate having a flat, inner pressing surface and being pivotably attached to one side of the base portion.

5 Claims, 3 Drawing Figures

CUTTING INSTRUMENT FOR A ROOT CANAL FILLER IN DENTAL TREATMENT

BACKGROUND OF INVENTION

This invention relates to a cutting instrument for a root canal filler used in dental treatment. More particularly, it is concerned with a root canal filler cutting instrument of a construction such that on the upper surface of a base portion are formed slots in which root canal fillers are to be fitted, the root canal fillers being held in place by an inner pressing surface of a cover plate which is attached to the base portion so as to facilitate the cutting operation for the root canal fillers, and the slots being graduated to facilitate the dimensioning of the root canal fillers to be cut.

If the hard tissue of a tooth is decalcified due to a decayed condition of the tooth and the decay becomes worse until it reaches the dental pulp, the latter will inflame and result in pain. To treat the tooth decayed to such an extent the dental pulp is extracted and thereafter a root canal filler is inserted up to the apica in an air-tight manner. The treatment which follows extraction of the dental pulp is generally called root canal treatment. If the decayed tooth is left as it is without receiving the above-mentioned treatment, the dental pulp will finally lose its life and consequently the pain will be allayed, but thereafter the dental pulp will develop into an infected root canal, which usually results in the formation of a diseased condition at the apica. The treatment at this stage is specially called infected root canal treatment, in which the interior of the root canal is cleaned mechanically and chemically followed by root canal filling. Thus, the root canal filling is the basis of clinical dentistry. Unless the root canal filling is made correctly, a dead space will be formed within the root canal and the peripheral tissue of the apica will be damaged; and in the worst case it may lead to the extraction of the tooth, and thus the clinical progress after treatment is seriously influenced. Root canal filling materials used at present are metallic or semi-hardened fillers having thicknesses standardized in conformity with root canal treating utensils. But the operation for adjusting a root canal filler into a desired length, namely the length of root canal (usually operation length) is very troublesome. Specially, the molar tooth portion usually has three canals, so when root canal fillers of different lengths and thicknesses must be provided at the same time, the operation has heretofore been very troublesome. In view of such circumstances there has been a demand for providing, in a short time, root canal fillers of required thicknesses and lengths calculated from the time of root canal treatment which precedes the root canal filling, to thereby improve the treatment efficiency and the accuracy of root canal filling.

This invention can almost satisfy the above-mentioned demand.

SUMMARY OF INVENTION

It is an object of this invention to provide a cutting instrument capable of easily cutting a root canal filler, which instrument includes a base portion on the upper surface of which is formed a slot for receiving a root canal filler, and further includes a cover means which is pivotably attached to one side of the base portion and provided with an inner pressing surface for pressing and fixing the root canal filler placed in the slot of the base portion.

It is another object of this invention to make it possible to simultaneously cut root canal fillers of various standardized thicknesses by forming a plurality of slots on the upper surface of the base portion so that the slots have various widths corresponding to such various standardized thicknesses of root canal fillers which are in conformity with root canal filling utensils, and placing root canal fillers of desired thicknesses in the slots of predetermined widths.

It is a further object of this invention to make it possible to adjust the length of root canal fillers easily and accurately by graduating the slots formed on the upper surface of the base portion.

It is a still further object of this invention to make it possible to cut root canal fillers at the same time when they are pressed and fixed with cover means, by providing the cover means with a cutting tool integrally.

DETAILED DESCRIPTION OF INVENTION

Figure 1:
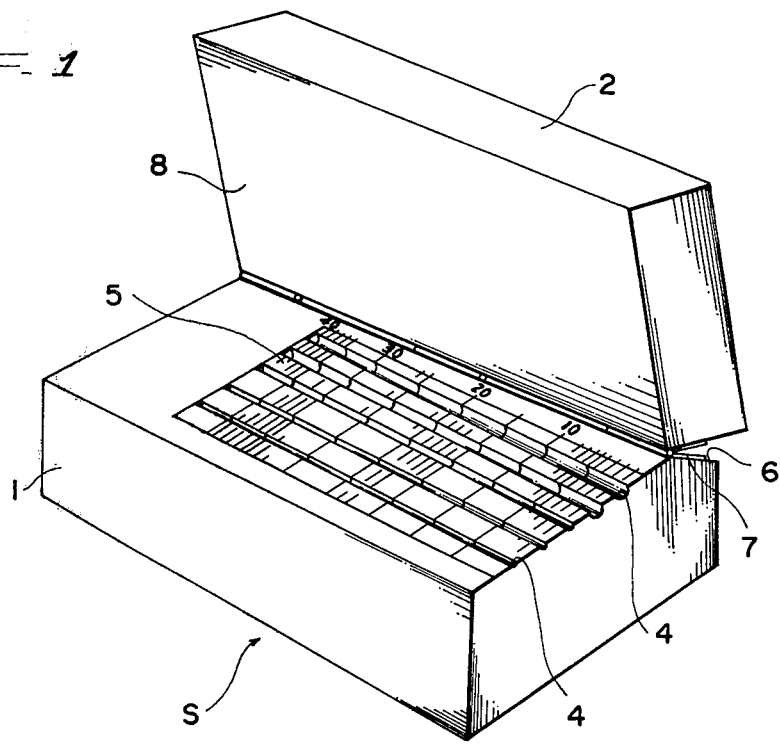
FIG. 1 is a perspective view of a cutting instrument according to one embodiment of this invention, with the cover means opened.
Figure 2:
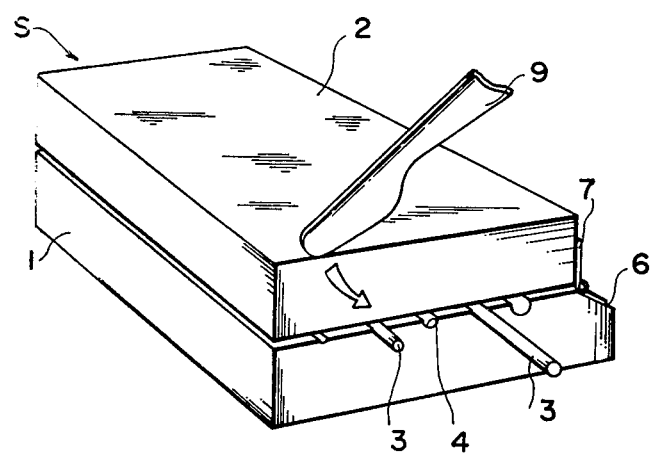
FIG. 2 is a perspective view of the cutting instrument in use with the cover means closed.

A cutting instrument, which is indicated with the letter S, has a base portion 1 and cover means 2 which is pivotably attached to one side of the base portion 1. On the upper surface of the base portion 1 are formed slots 4 to receive therein root canal fillers 3, the slots 4 having a scale 5.

The upper surface of the base portion 1 is a level surface except one side portion thereof which is inclined to form an inclined surface 6, to which is attached the cover means 2 through a pivotal hinge 7 so as to permit opening and closing of the cover means 2. The cover means 2 has a flat, inner pressing surface 8 whereby the root canal fillers 3 in the slots 4 are pressed and fixed when the cover means 2 is closed.

The slots 4 are formed from one side end toward the opposite side of the upper surface of the base portion 1 so that at least one end of the root canal fillers 3 in the slots 4 projects outwardly from the base portion 1.

A plurality of the slots 4 formed on the upper surface of the base portion 1 have various widths corresponding to various standardized thicknesses of the root canal fillers 3 which are in conformity with root canal filling utensils. The slots 4 have respective depths such that the other peripheries of the root canal fillers 3 are exposed to the upper surface of the base portion 1.

The plural slots 4 are formed side by side in the order of the size of slot width and they are of a depth to the extent that the portions of the root canal fillers 3 exposed from the slots 4 are of uniform height from the upper surface of the base portion 1 so that when the cover means 2 is closed the plural root canal fillers 3 in the plural slots 4 can be pressed and fixed simultaneously and uniformly.

Accordingly, to operate the cutting instrument S of this invention so as to obtain root canal fillers of desired thicknesses and lengths, the cover means 2 is opened and the standaridzed root canal fillers 3 are placed in the slots of widths corresponding to the thicknesses of the fillers 3, then the fillers 3 are moved within the slots 4 with reference to the scale 5 until they are adjusted to the desired lengths. The cover means 2 is then closed and the extra lengths of the root canal fillers 3 projecting from one side of the base portion 1 are cut along the one side by means of a cutting tool 9 such as a surgeon's knife while pressing and fixing the root canal fillers 3 with the pressing surface of the cover means 2. Since the opening of the cover means 2 is angularly controlled by the inclined surface 6 of the base portion 1, the opening and closing operation of the cover means 2 can be done with one hand without producing oscillation of the base portion 1.

Figure 3:
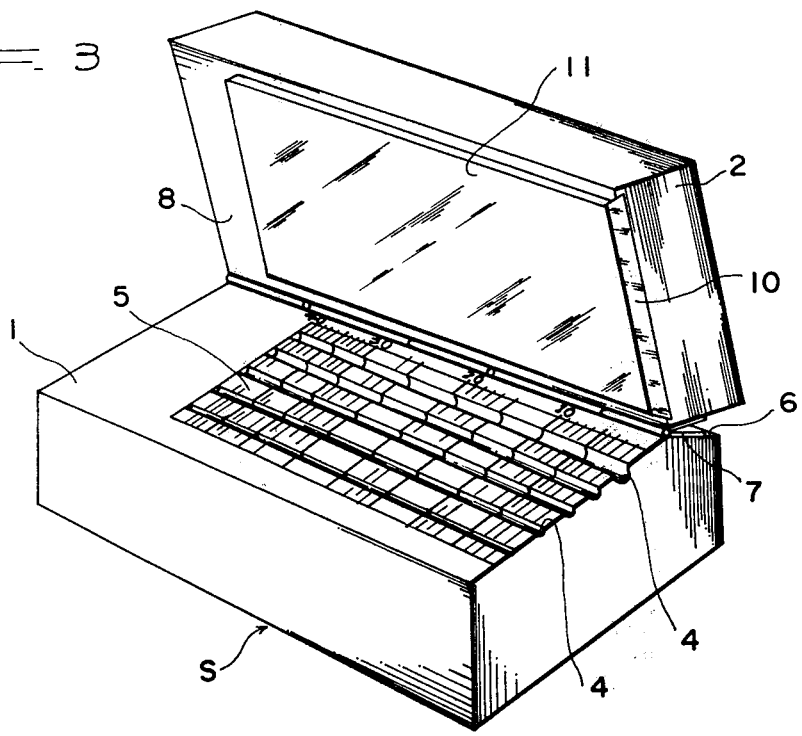
FIG. 3 is a perspective view of a cutting instrument according to another embodiment of this invention, with the cover means opened.

FIG. 3 illustrates another embodiment of this invention, in which a cover means 2 of a similar construction as in the foregoing cutting instrument S has an integrally-attached cutting tool 10 on one side thereof, namely the side from which projects an extra length of each root canal filler 3, whereby when the cover means 2 is closed the extra lengths of the root canal fillers 3 can be cut with certainty, resulting in simplification of the cutting operation.

A buffer plate 11 made of an elastic material such as rubber may be attached to the pressing surface 8 of the cover means 2 whereby the fixation of the root canal fillers 3 by the cover means 2 can be made more certain; besides, the root canal fillers can be prevented from being deformed by the pressure of the cover means 2.

Consequently, the use of the cutting instrument of this invention constructed as above is advantageous in that the adjustment of the length of root canal fillers, which heretofore has been troublesome, can be made easily and quickly, and in that plural root canal fillers of different thicknesses can be simultaneously adjusted in length and cut, so that a great contribution is expected to the improvement in efficiency of root canal treatment, etc.

What is claimed is:

1. A cutting instrument for a root canal filler in dental treatment, comprising a base portion and cover means pivotably attached to one side of said base portion, said base portion being provided on its upper surface with a slot to receive therein a root canal filler, said slot being graduated for dimensioning the root canal filler, and said cover means having a pressing surface for pressing and fixing the root canal filler placed in said slot.

2. A cutting instrument as defined in claim 1, in which said slot formed on the upper surface of said base portion extends from one side end toward the opposite side of said base portion so that an extra length of the root canal filler projects outwardly from the base portion, and said slot has a width corresponding to a standardized thickness of the root canal filler and further has a depth such that part of the outer periphery of the root canal filler is exposed to the upper surface of said base portion.

3. A cutting instrument as defined in claim 1, in which a plurality of slots are disposed side by side on the upper surface of said base portion, said slots having a variety of respective widths corresponding to various standardized thicknesses of root canal fillers and further having respective depths such that the exposed portions of the root canal fillers are at the same and constant height from the upper surface of said base portion.

4. A cutting instrument as defined in claim 1, in which said cover means is provided with a buffer plate made of an elastic material such as rubber, said buffer plate being mounted on said pressing surface which forms an inner surface of the cover means.

5. A cutting instrument as defined in claim 1, in which said cover means is provided with a cutting tool integrally on a side portion thereof on the side of the instrument from which projects an extra length of the root canal filler.

* * * * *